United States Patent
Chang et al.

(10) Patent No.: US 10,292,797 B2
(45) Date of Patent: May 21, 2019

(54) ORAL CARE APPLIANCE USING PULSED FLUID FLOW

(71) Applicant: KONINKLIJKE PHILIPS N.V., Eindhoven (NL)

(72) Inventors: Yu-Wen Chang, Mercer Island, WA (US); Gregory Russ Goddard, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 814 days.

(21) Appl. No.: 14/774,178

(22) PCT Filed: Mar. 10, 2014

(86) PCT No.: PCT/IB2014/059569
§ 371 (c)(1),
(2) Date: Sep. 10, 2015

(87) PCT Pub. No.: WO2014/141027
PCT Pub. Date: Sep. 18, 2014

(65) Prior Publication Data
US 2016/0022392 A1    Jan. 28, 2016

Related U.S. Application Data

(60) Provisional application No. 61/787,692, filed on Mar. 15, 2013.

(51) Int. Cl.
*A61C 17/02* (2006.01)
*A61C 17/022* (2006.01)
*A61C 17/028* (2006.01)

(52) U.S. Cl.
CPC ........ *A61C 17/0202* (2013.01); *A61C 17/022* (2013.01); *A61C 17/028* (2013.01); *A61C 17/0217* (2013.01)

(58) Field of Classification Search
CPC . A61C 17/0202; A61C 17/022; A61C 17/028; A61C 17/0217
See application file for complete search history.

(56) References Cited

U.S. PATENT DOCUMENTS

2008/0255498 A1  10/2008  Houle
2011/0027746 A1   2/2011  McDonough et al.

FOREIGN PATENT DOCUMENTS

| | | |
|---|---|---|
| JP | 2000157562 A | 6/2000 |
| WO | 2007025244 A2 | 3/2007 |
| WO | 2010055434 A1 | 5/2010 |
| WO | 2011077291 A1 | 6/2011 |
| WO | 2012042445 A1 | 4/2012 |

*Primary Examiner* — Sundhara M Ganesan (57) ABSTRACT

An oral care appliance comprises: a fluid pump assembly (46); a source of liquid (50); and a source of gas (12), wherein the pump is in operative communication with the sources of liquid and gas to produce a series of gas-injected fluid pulses, directed to a nozzle assembly (80) from which the resulting pulses are directed to the teeth. The individual pulses have a pulse width in the range of 0.001-0.5 seconds, a pulse height from 0.1-10 Newtons, and a rise/fall time range of 0.5-250 ms, a repetition rate in the range of 2 Hz to 20 Hz. The gas/liquid mixture range from 40-95% volume to volume, gas to liquid.

5 Claims, 6 Drawing Sheets

ORAL CARE APPLIANCE USING PULSED FLUID FLOW

CROSS-REFERENCE TO PRIOR APPLICATIONS

This application is the U.S. National Phase application under 35 U.S.C. § 371 of International Application No. PCT/IB2014/059569, filed on Mar. 10, 2014, which claims the benefit of U.S. Provisional Patent Application No. 61/787,692 filed on Mar. 15, 2013. These applications are hereby incorporated by reference herein.

TECHNICAL FIELD

This invention relates generally to apparatus for cleaning teeth using a combination of bursts of gas and bursts of fluid to produce a desired gas/fluid mix, and more particularly concerns a single assembly for producing both gas bursts and fluid bursts in coordination, as well as an assembly for producing a jet pattern of gas and fluid in another embodiment.

BACKGROUND OF THE INVENTION

In systems which produce teeth cleaning with a combination of bursts of gas and fluid, such as water, it is important that the gas and fluid are mixed in a way to deliver the greatest efficacy of cleaning. In addition it is important to coordinate the timing of these two functions while still being relatively simple in structure and operation, and sufficiently small to fit within a specific device footprint. Use of separate liquid and gas delivery systems typically have some problems with timing, as well as space constraints and the need for dual power sources.

SUMMARY OF THE INVENTION

Accordingly, the oral care appliance comprises: a fluid pump assembly; a source of liquid; a source of gas, wherein the pump is in operative communication with the sources of liquid and gas to produce a series of gas-injected fluid pulses, directed to a nozzle assembly from which the resulting pulses are directed to the teeth, wherein the individual pulses have a pulse width within the range of 0.001-0.5 seconds, a pulse height from 0.1-10 Newtons, a rise/fall time range of 0.5-250 ms, a repetition rate in the range of 2 Hz to 20 Hz, and wherein the gas/liquid mixture range from 40-95% volume to volume, gas to liquid.

DETAILED DESCRIPTION

FIGS. 1-5 show one embodiment of an apparatus, generally at 10, for producing successive bursts of gas and liquid, such as water, which mix to produce a stream of gas and liquid droplets used for cleaning teeth, especially the interproximal areas of the teeth, accomplishing a "flossing" function. The term gas used herein can include air or other gases or mixtures. Apparatus 10 forms the major part of a complete teeth cleaning appliance, the exterior of which is shown in FIG. 6 and described in more detail below.

Figure 1:
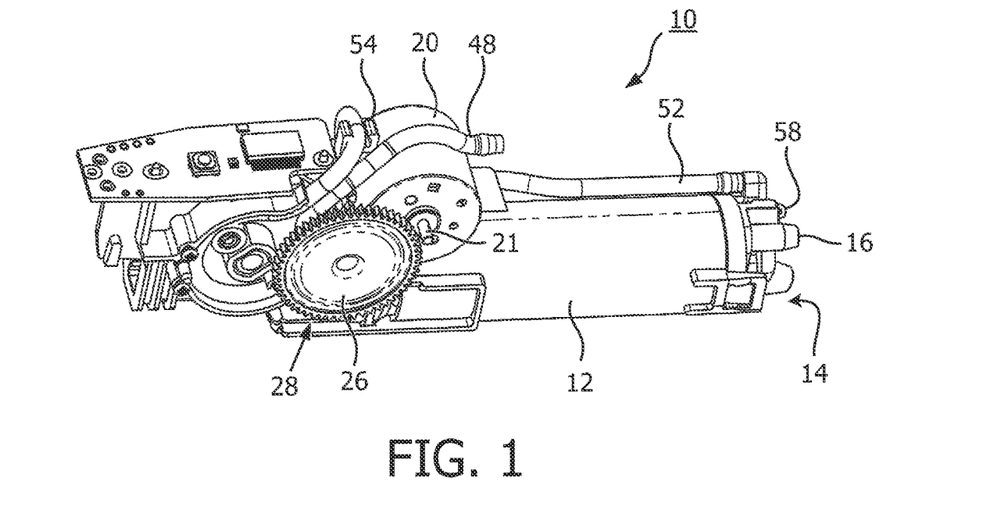
FIG. 1 is a perspective view showing the apparatus.
Figure 2:
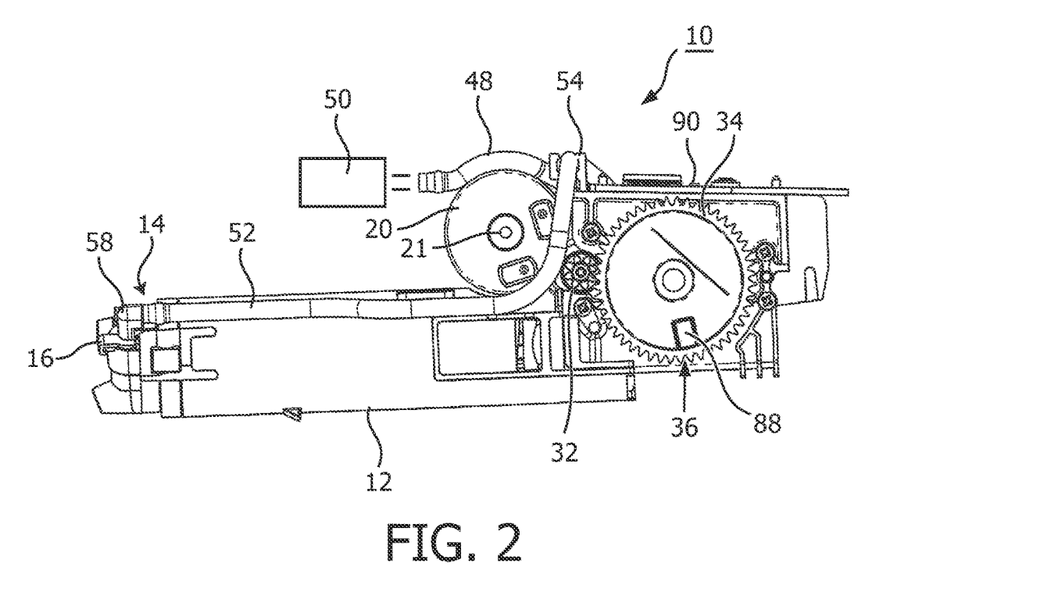
FIG. 2 is an elevational view of the opposing side of the apparatus of FIG. 1.

Referring now specifically to FIGS. 1 and 2, apparatus 10 includes an gas cylinder 12, which in the embodiment shown is approximately 2.5 inches long with an internal diameter of 0.5-1.0 inches. At a distal end 14 of gas cylinder 12 is a nozzle 16 through which a mix of water or other liquid bursts and fluid, typically gas, exit, in the form of a stream of high velocity liquid droplets. The liquid droplets are directed toward the teeth of a user, particularly the interproximal area, for cleaning.

Figure 3:
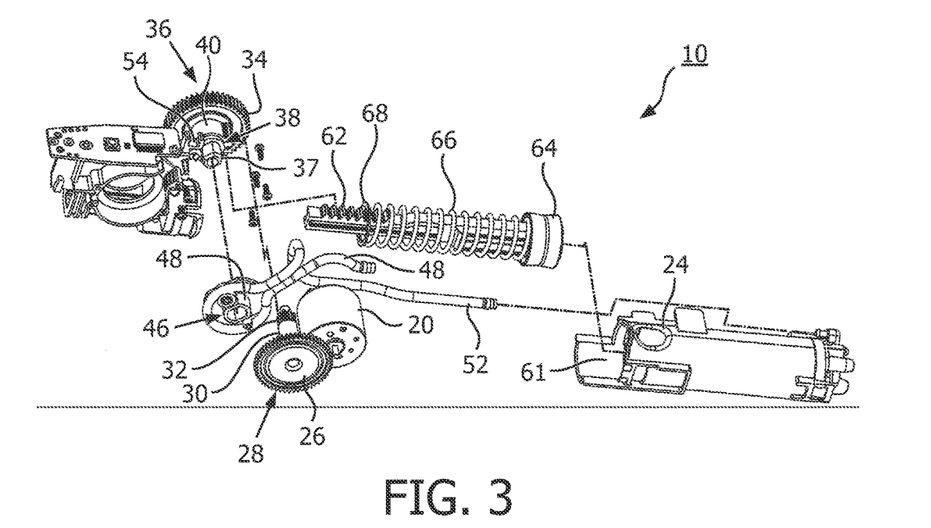
FIG. 3 is an exploded view of the apparatus of FIG. 1.
Figure 4:
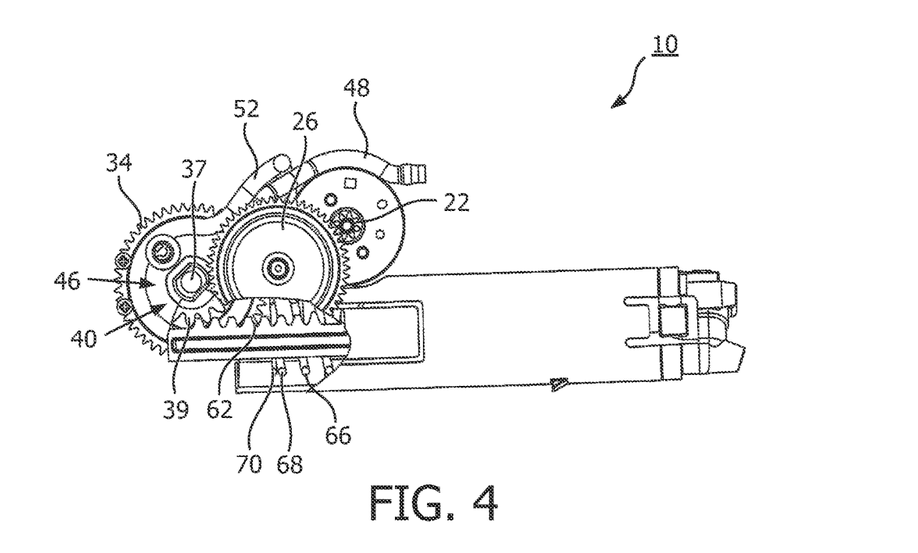
FIG. 4 is a partially cutaway elevational view of FIG. 1.

The apparatus includes a motor 20 which in the embodiment shown is a DC motor, typically with high torque, e.g. 15 Newton meters, although this value is typically achieved after gear reduction. The motor itself thus does not have to produce such a value of torque itself. Such motors are widely commercially available. Various motors are suitable. Motors made by Mitsumi are for instance examples of a suitable motor. Motor 20 includes an output shaft 21 on which is mounted a motor drive gear 22 (FIG. 4). In the embodiment shown, there are 8 teeth on the motor drive gear. The number of teeth on gear 22, as with the number of teeth on the other gears, can be varied. Motor 20 is positioned at 24 at the rear upper surface of gas cylinder 12. Motor drive gear 22 engages a first (outer) gear part 26 of a first compound gear 28 located at a first side of the apparatus. The first compound gear 28 in the embodiment shown is made of plastic as are the other gears, however it could be made of other material as well. The first gear part 26 of gear 28 in the embodiment shown has 53 teeth. The motor drive gear 22 in operation rotates it in a clockwise direction. The first compound gear 28 also includes a gear shaft 30 and a second (inner) gear part 32 coincident with the distal end of shaft 30, as shown in FIG. 3. In the embodiment shown, the second gear part of the first compound gear has eight teeth.

The shaft 30 with the second gear part 32 of the first compound gear 28 extends through apparatus 10 and mates with a first (outer) gear part 34 of a second compound gear 36 positioned on an opposing side of the apparatus. In the embodiment shown, the first gear part 34 of the second compound gear has 48 teeth, although this can be varied, as noted above. A second (inner) gear part 38 of second compound gear 36 is positioned adjacent the first gear part 34 on a center gear shaft 37. The second gear part of the second compound gear has two parts, a first part comprising a partial set of 8 teeth referred to at 39 spaced around approximately one-half of the circumference of the second gear part and a second part 40 which has no teeth, i.e. the surface is smooth at the base of the teeth portion of the second gear part. Typically, but not necessarily, the two parts are each one-half of the second gear part.

The second compound central gear shaft 37 extends back through the apparatus to the first side of the apparatus and engages a peristaltic fluid pump assembly 46, which includes a pump 48. Peristaltic pump assembly 46 includes a first tube section 48 which extends to a fluid reservoir 50. In the embodiment shown, the fluid in reservoir 50 is water, although other fluids can be used as well. These include various formulations which assist in cleaning teeth, such as chlorhexidine, hydrogen peroxide-based rinses, mixtures of water, baking soda, essential oils or mouthwash, for example. The peristaltic pump assembly 46 also includes a second tube 52 which extends from the pump and above the body of the apparatus, in a U-shaped mounting element 54, and then along the outer surface of the gas cylinder to a mixing chamber 58 on the distal end of the gas cylinder.

The second gear part 38 of the second compound gear 36 mates with a linear rack member 62 which is positioned at a proximal end 61 of gas cylinder 12. In the embodiment shown, rack member 62 is approximately 2 inches long and includes a set of 8 spaced teeth on the upper surface thereof. The distal end of rack member 62 includes a seal member 64 which mates in a fluid tight relationship with the interior surface of gas cylinder 12. Extending from the distal end of rack 62 at seal 64 and encircling the rack along most of the length thereon is a compression spring 66. The proximal end 68 of spring 66 is positioned against a stop element 70 in body portion 20, as shown in FIG. 4.

Figure 5:
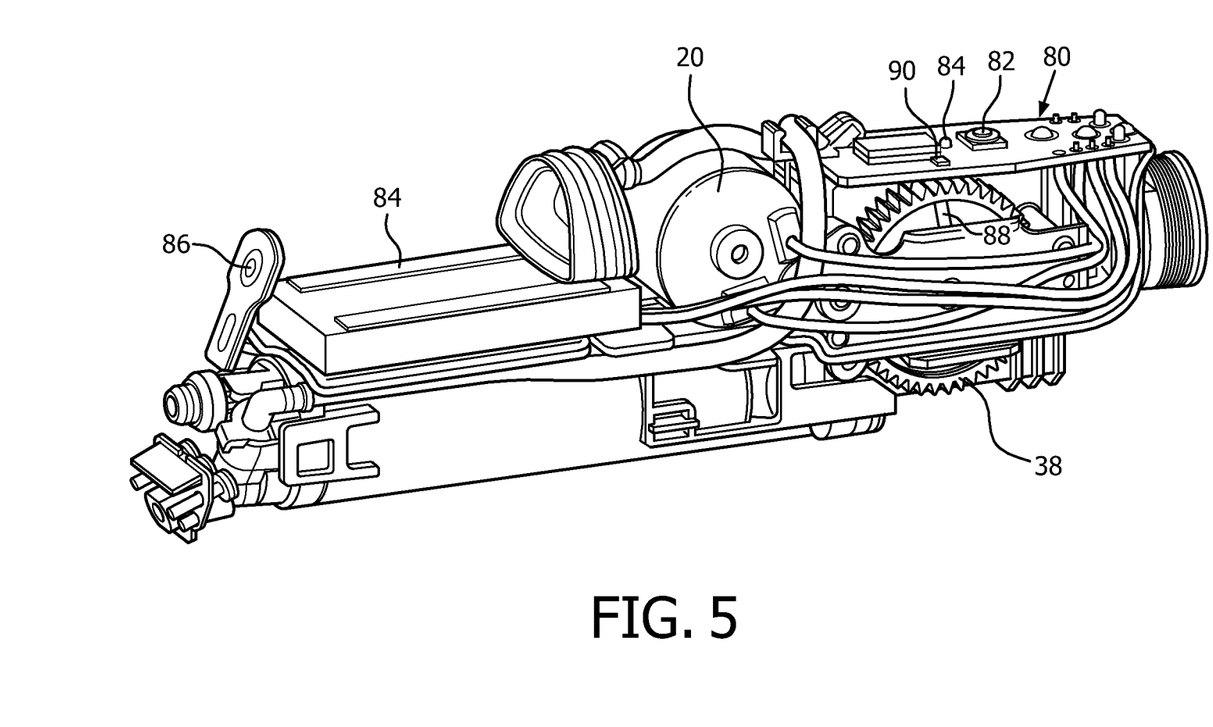
FIG. 5 is a perspective view of the apparatus showing the opposing side of the apparatus, similar to FIG. 2.
Figure 6:
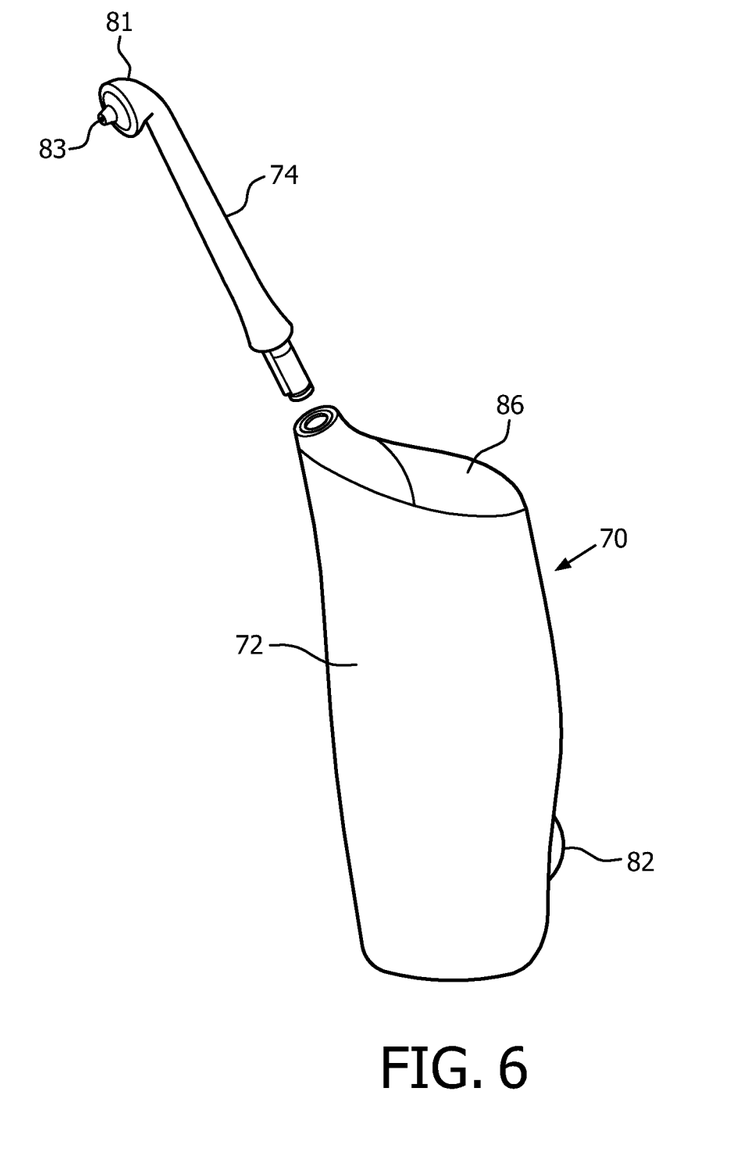
FIG. 6 is a perspective exterior view of an appliance incorporating the apparatus of FIGS. 1-5.

FIG. 5 is similar to FIG. 2, showing motor 20, and the second compound gear 36, specifically, the second gear part 38 thereof. FIG. 5 also shows a microprocessor controller 80, in the form of a printed circuit board, for the apparatus, which controls all of the operations thereof and is mounted on an internal frame portion of the apparatus. FIG. 5 also shows an on/off power button 82 for the appliance which enables the operation of the appliance by connecting battery 84, which in the embodiment shown is a lithium-polymer battery, to motor 20. When the on/off button 82 is on, a power light comes on. The appliance also includes an actuation button 86 which, when operated by a user, produces a single shot (burst) of the liquid/gas mixture out the nozzle end 16 of the appliance.

In operation, in general, as the motor drive gear 22 turns, rack 62 moves rearwardly by action of the partial set of teeth 39 of the second gear part of the second compound gear 36, the rack moving relatively away from the proximal end 61 of the gas cylinder, compressing spring 66 against stop 70. Gas enters the gas cylinder through an opening at distal end 14 thereof. In the embodiment shown, spring 66 undergoes 30 mm of compression. Spring 66 in typical operation is compressed successively every 400 to 900 milliseconds, depending on the precise rpm of the motor and the action of the control assembly. It is possible to operate faster than every 400 ms, even down to 100 ms.

When the second compound gear 36 rotates so that the no-tooth gear portion 40 of the second gear part of compound gear 36 comes adjacent the rack, such that there is no longer a gear contact between the second gear part and the rack, and hence no gear holding the rack in position, spring 66 operates to move the rack quickly forwardly, moving the sealed end of the rack forwardly in the gas cylinder, forcing a burst of gas into the mixing chamber, along with a liquid (water) burst, produced concurrently by action of the pump 68 or somewhat prior, driven by shaft 37 of the second compound gear. Typically, there is one shot of gas per revolution of the motor shaft, every 400-900 milliseconds (or faster); further, there is approximately 0.15 ml of fluid provided to the mixing chamber per revolution of the motor shaft.

More particularly, in the start sequence of operation, with the power button 82 in an on condition, activation button 84 is pressed by the user. This begins the intake stroke of the apparatus. In the starting position, rack member 62 and the seal 64 are fully forward, with the partial set of teeth 39 of the second gear part of the second compound gear just engaging the rear end of the rack member 62. Motor 20, as indicated above, initiates action of the entire gear train, resulting in the rack member 62 moving rearwardly and seal 64 retracting in the gas cylinder. This results in compression of spring 66, and the pulling of gas into the gas cylinder. As the motor and the gear train operates, peristaltic pump assembly 46 operates, causing pump 48 to move fluid, such as water, into the mixing chamber of the apparatus. The outer gear part 34 of second compound gear 36 includes a magnet 88 (FIG. 5) on an outer surface thereof. As gear 34 rotates, a Hall Effect sensor 90 positioned on the internal frame portion of the appliance detects the magnet as it moves past the sensor, and in response starts a software implemented delay time present in controller 80, which turns off motor 20 at the end of the time. The timing of the software delay is established such that motor 20 is not shut off until after the start of the exhaust portion of the operating cycle.

In the exhaust portion of the cycle, when rack 62 and seal 64 are pulled to their rearmost position, with spring 66 fully compressed against stop 70 by the action of the partial set of teeth 39, further rotation of the second compound gear by action of the motor results in the non tooth portion 40 of the second gear part 38 coming adjacent the rack so that there is a disengagement between the second gear part 38 and the rack. Rack 62 and seal 64 move quickly forward, driven by the release action of spring 66. The gas in the gas cylinder is forced rapidly out of the cylinder into the mixing chamber where it mixes with the liquid present therein. The resulting liquid/gas mix, in the form of a single burst, is then forced out of the nozzle.

The Hall Effect sensor software delay times out and the motor is shut off. The momentum in the gear train allows the second gear part 38 of the second compound gear 36 to continue to rotate until the partial set of teeth 39 initially engages with the first tooth or so of the rack 62. This small amount of rotation results in some water being moved into the mixing chamber by the continued action of the peristaltic pump. The total volume of water provided for each shot is the amount of water provided by a full 360° rotation of the peristaltic pump 48.

At this point, the apparatus is now in a condition to begin the next shot/burst. The gear train at the end of each operating sequence stops in the same position after each burst, in accordance with the software timer action operating the motor. The delay timer also acts to prevent the user from operating the unit too rapidly and overheating the motor. It prevents the start of another operating sequence, even though the activation button 84 is pressed. At the end of the delay time, pressing the activation button will initiate action of the apparatus, producing a successive burst of liquid/gas mixture.

The successive bursts of gas and liquid are brought together in the mixing chamber 58, with proper, consistent timing, from which the resulting mixture exits through port 16, directed through the nozzle assembly toward the teeth of the user for cleaning thereof.

FIG. 6 shows the exterior of such an appliance 70. It includes a handle/receiver portion 72 and an extending nozzle portion 74. Located in the handle/receiver portion 74 is a liquid/gas mixture burst-generating system and a power source therefor, as shown in FIGS. 1-5 above. Nozzle portion 74 extends away from the handle and is relatively slim, in order to conveniently fit into the mouth of a user, for reaching all of the interproximal and gingival areas of the teeth. The nozzle portion terminates in a nozzle exit member 81 having a small opening 83 in a forwardly extending portion, through which the successive bursts of liquid/gas mixture are directed to the teeth. The opening in the embodiment shown is approximately 1 mm in diameter, although this can be varied. Further, exit member 81 has a surface configuration to facilitate proper contact and placement of the exit member in the interproximal areas of the teeth. The handle/receiver includes an on/off switch 82 and a control member 86 which when operated by the user produces the bursts of liquid/gas mixture. While the liquid will frequently will be water, it should be understood that other liquids, such as mouthwash and medications, can also be utilized.

Figure 7A:
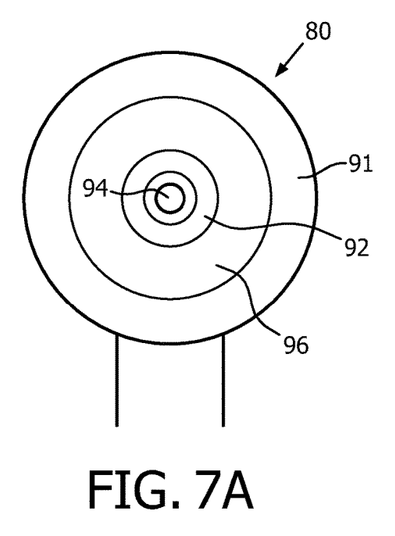
FIG. 7A is a front elevational view of the nozzle assembly portion of FIG. 6.
Figure 7B:
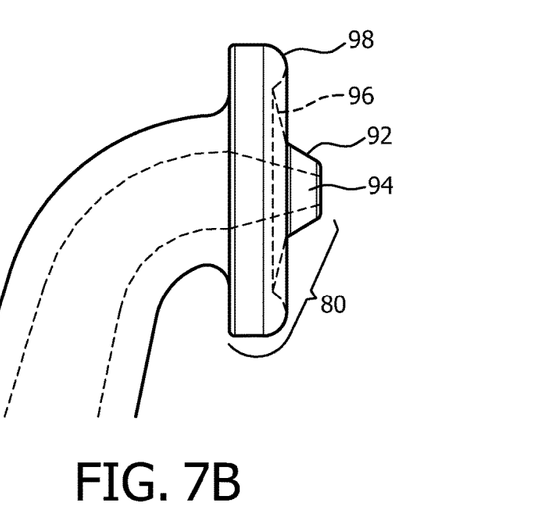
FIG. 7B is a cross-sectional view of the nozzle assembly of FIG. 7A.
Figure 8:
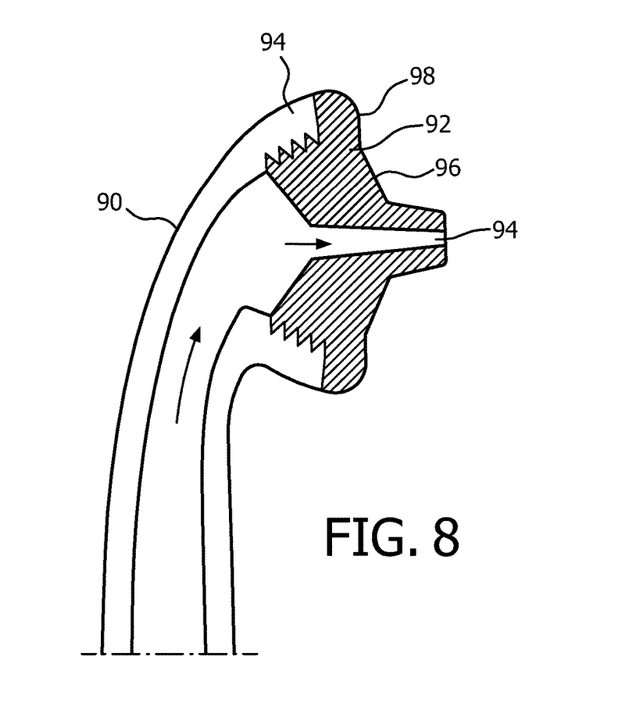
FIG. 8 is another cross-sectional view of an exit portion of a nozzle assembly.

In FIGS. 7-8, an elongated nozzle portion which terminates in a nozzle exit member 80 is shown in more detail, including a base portion 91 and a tip portion 92. At the center of tip portion 92 is an exit opening 94 through which high velocity droplets are delivered to the teeth of the user for cleaning when the appliance is positioned properly by the user in the mouth. The nozzle exit member is generally configured to provide a guidance function for the interproximal areas. The tip portion 92 extends above a surrounding intermediate portion 96 by approximately 1-3 mm. In some cases, the exit nozzle member can be slightly tapered, with an exterior diameter of approximately 2 mm. The intermediate trough portion 96 tapers slightly away from exit member 24. The intermediate portion 96 terminates in a boundary portion 98 which has a curved upper surface which defines a lip for the tip portion 92. Additional details and advantages of such a structure are set forth U.S. Application 61/289,589, which is owned by the assignee of the present invention, the contents of which application are hereby incorporated by reference.

In one embodiment, a tip portion 98 of the nozzle assembly 80 is separable from a base portion 94 thereof which extends from body 12. This is shown in FIG. 8. The tip portion is replaceable. The replaceable tip portion of the nozzle has a number of advantages. These include the ability to replace the tip of the nozzle due to wear. It also permits nozzle variations depending on a desired hardness, (or softness) of the material. Further, the diameter of the exit orifice of the tip portion can be changed to alter the characteristic of the liquid droplet spray.

Figure 9:
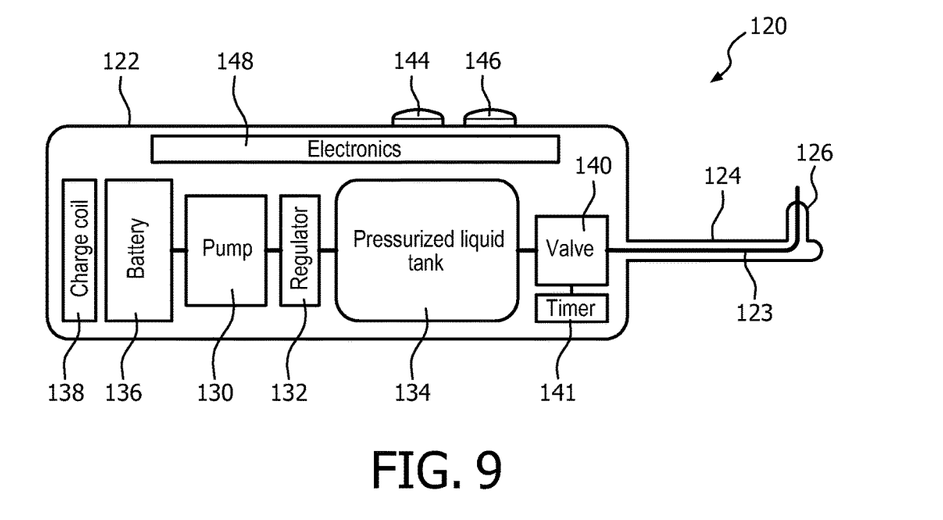
FIG. 9 is a simplified view of an alternative arrangement to that of FIGS. 1-6.

FIG. 9 shows a fluid-based cleaning appliance, generally at 120. FIG. 9 shows a more generalized system, capable of providing a spray output, a pulse output or a jet output producing bursts of gas at selective frequencies, under control of a microprocessor. Typically the fluid is water, although it could be other liquids, including medications or mouthwash. The appliance 12 includes an appliance body 122, which includes a fluid delivery system for producing discrete bursts of gas/fluid mixtures, including sprays, bursts and jets, and an outlet for the fluid bursts which proceed through a fluid delivery path 123 in an outlet member 124, at the end of which is a nozzle assembly 126, as described above, which could include a single nozzle or a plurality of nozzles. The discrete fluid bursts from nozzle 126 are sufficient to effectively manage biofilm through mechanical removal thereof, with a resulting reduction in the virulence of microorganisms in the mouth. The discrete fluid bursts provide a cleansing benefit greater than toothbrush bristles alone, because the fluid bursts are able to reach between the teeth and along the gum line where bristles cannot reach.

The use of discrete i.e. separate, bursts of fluid, as opposed to a continuous or pulsed jet of fluid, does result in substantially less total liquid volume per brushing event, which may be an advantage as it enhances user comfort and compliance, while maintaining effectiveness. The cleaning event is typically two minutes.

The delivery system includes a displacement pump 130, which is programmed in combination with a regulator 132, to provide discrete bursts of liquid, typically water, as indicated above, from a tank 134. The liquid could be various medications or mouthwashes. The regulator 132 maintains the pressure in the water tank 134 at a specified level. Typically, the pressure is in the range of 40-120 psi, with a preferred range of 70-112 psi. The water tank holds a cleansing event amount of liquid, slightly less than 0.2 ml. It has been discovered that a user can readily tolerate this amount of liquid in a normal cleansing event of two minutes. The appliance also includes a battery 136, which operates pump 130, and a conventional charger coil 138, which is used with a charging member (not shown). Controlling the release of liquid from the water tank is a valve 140, which is for instance a solenoid valve, and a timer 141. The appliance also includes a power button 144 and a firing button 146, although those two functions can be combined in a single element. A microcontroller 148 controls the operation of the appliance, including an automatic mode of operation for the appliance. The microcontroller can control various fluid dynamics parameters, as discussed in more detail below. This is an alternative to the pump/controller system of FIG. 1.

The discrete fluid bursts are predefined in terms of time duration and firing rate. In a manual mode, the bursts are generated by operating firing button 146. Timer 141 controls the duration of the fluid bursts. In one embodiment, the burst time duration range is 0.02-2 seconds, with a preferred time duration of 0.05-0.2 seconds. The firing rate in a manual mode is controlled by the user, which is typically significantly longer than the burst duration.

In automatic mode, which is controlled by microcontroller 148, the time duration of the liquid burst will be the same as in the manual mode. The automatic mode may be initiated by a programmed sequence of operating the on-off switch or by a separate switch member/button for the user to operate. The firing rate can be automatically controlled or pre-programmed, typically, 0.1-2 seconds, with a preferred range of firing rate of 0.5-1.5 seconds. In some cases, the time duration of the burst and the firing rate may be adjusted by the user by a predefined sequence of operating the on-off switch. In other cases, the firing rate is permanently set during manufacture.

The advantage of the present system is that the discrete fluid bursts produced by the system of FIG. 9 provides effective cleaning for the teeth and effective treatment of the gum tissue, but with the total volume of liquid being comfortable for the user with a typical cleansing event time of two minutes, which is an encouragement for regular use.

Figure 10:
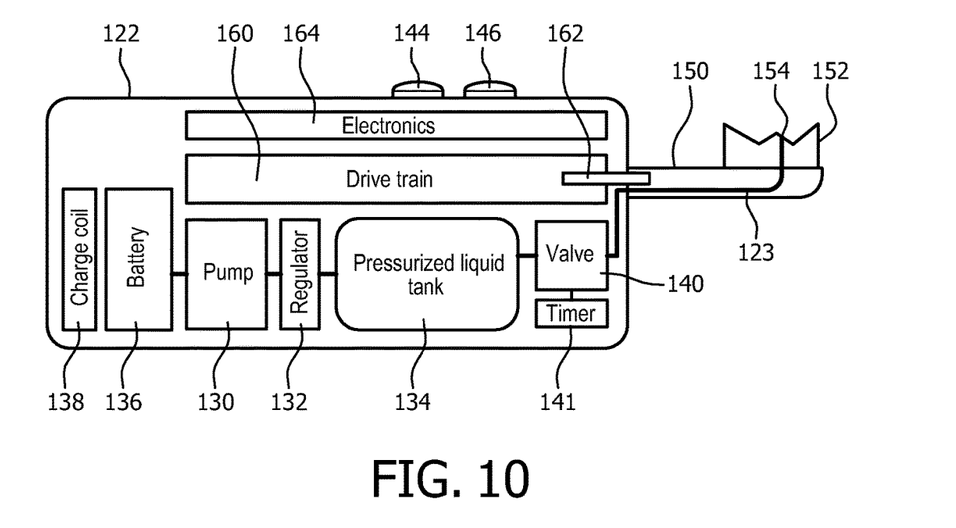
FIG. 10 is a simplified view of an appliance using the apparatus of FIG. 1-6 or 9 with a power toothbrush.

FIG. 10 shows a variation of the embodiment of FIG. 9, with the appliance having a similar fluid delivery arrangement thereto, or the specific system of FIGS. 1-6 but with the addition of outlet member 150 being driven in a desired physical movement, such as a back-and-forth oscillatory action, with a set of bristles 152 being positioned at the end of the outlet member. Nozzle 154 or nozzles will typically be positioned within the set of bristles 152, but hollow bristles could provide the nozzle action. The appliance will include a drive train assembly 160, with a drive shaft 162 extending therefrom to drive outlet member. The drive train is controlled by microcontroller 164. The drive arrangement could be a resonant toothbrush action at a frequency in the range of 230-260 Hz for instance.

Fluid delivery, gas delivery, fluid/gas mixing and the nozzles described above can all be varied as follows:

Fluid pumps can include peristaltic, diaphragm, rotary, impeller, electroosmotic, gear, microannular, cyclone or via a pressurized gas/pneumatic cylinder/container, either positively or negatively pressure driven. Fluid can be passively pulled in through a venturi or via the Bernoulli effect into a nozzle.

Gas pumps can include peristaltic, diaphragm, rotary, impeller, electroosmotic, gear, microannular, cyclone or gas can be moved directly from a pressurized gas "tank", either positively or negatively driven. Gas can be passively pulled in through a venturi or via the Bernoulli effect over an orifice.

The gas and fluid mixing can be achieved through a tortuous path channel, array or orifices, a string of periodic/aperiodic orifices, dynamic elements or through direct phase control driving of the pumps (fluid or gas).

Various nozzles can be used, including any of the elements to create pulsation or gas/fluid mixing through tortuous paths, with the inner and outer dimensions of the part and direction changes within the fluid/gas/aerosol path.

For optimal plaque removal and for corresponding oral health benefits, the shear stress provided on the biofilm must exceed the elastic and plastic deformation points of plaque and in addition overcome the adhesive action within the biofilm itself and/or the adhesive forces holding the biofilm to the dental surfaces. Accordingly, biofilm plaque has the following mechanical and viscoelastic properties which must be overcome: Young's modulus between 1 Pa and 50 kPa; shear modulus between 1.1 and 50 Pa; cohesive shear strengths between 2 and 50 Pa; adhesive strengths of 5-75 Pa or 0.05-1 J/m$^2$; tensile strengths between 0.1 Pa and 6 kPa; adhesion shear stresses of 0.1 to 0.65 J/m$^2$; storage moduli of 1-10 kPa; loss modulus between 0.1-3 nJ/μm$^3$; and failure strains of 150-320%. The above ranges depend on the type of the bacterial colony and age of the plaque and the other mechanical, chemical and physiochemical properties of the plaque on which it is positioned.

There are various fluid dynamic actions produced by the above appliances which are effective against biofilm on the teeth. One category of fluid dynamics involves a pulse-type fluid flow operation, which is a more turbulent type of fluid flow. The pulse operation utilizes the mechanics of FIGS. 1-5 and 9, which are capable of delivering a variety of pulsing liquid flows, producing gas pulses and fluid having various characteristics, which can include sputtering and spray. The particular fluid flow characteristics produced n this embodiment are produced by programming the microcontroller, but also by various mechanical characteristics of the nozzle assembly and the nozzle exit member. These include the characteristics of the exit orifices, the configuration of the fluid channel or variable surface characteristics of the fluid channel which interact with the flow. It can also include flexible membrane or various elastic elements within the flow.

In the pulse arrangement, the pulse pattern can include 1-10 pulses per pulse burst. The flow parameters of the individual pulses include pulse width, pulse height, rise/fall time, the number of sub-pulses, i.e. pulses within a larger pulse, and the repetition rate of the pulse. The pulse width ranges from 0.001 to 0.5 seconds. The pulse height ranges from 0.1 to 10 Newtons. Rise/fall time range from 0.5 to 250 ms, while the sub-pulses per pulse range from 1 to 5. Repetition rate ranges from 2 Hz to 20 Hz, while the gas-liquid mixture ranges from 40-95% by volume between gas and liquid.

Pulses can be created using dynamic elements consisting of elastic sections or orifices or similar elements which change their size, shape or flow profile in response to changes in flow rate or externally applied signals, such as memory metal, electroactive polymer, piezo or magnetostrictive effects, or direction pulsation of fluidic and/or gas driving pumps.

This embodiment can be used with incident angles from 0-90°, with 0 being parallel to the tooth surface. Also, a nozzle fan angle is 5-150°, with flow rates of 0.15 ml per shot, or within a range of 0.05-0.07. Delivery durations are 0.001-0.5 seconds, while the flow is described by Reynold's numbers between 100-10,000.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. An oral care appliance, comprising:
   a fluid pump assembly;
   a source of liquid;
   a source of gas, and
   a microcontroller wherein the fluid pump assembly is in operative communication with the sources of liquid and gas to produce a series of gas-injected fluid pulses output via at least one orifice of a nozzle exit assembly from which the series of gas-injected fluid pulses are directed to a user's teeth, and wherein the microcontroller is programmed to control an operation of the fluid pump assembly to produce individual pulses of the series of gas-injected fluid pulses effective against biofilm on teeth that have each individual pulse of the series of pulses has a pulse width within a range of 0.001-0.5 seconds, a pulse height from 0.1-10 Newtons, a rise/fall time range of 0.5-250 ms, at least one sub-pulse, a repetition rate in a range of 2 Hz to 20 Hz, and a gas/liquid mixture range from 40-95% volume to volume, gas to liquid.

2. The appliance of claim 1, wherein the series of gas-injected fluid pulses further comprise a pulsed liquid in a form of a spray.

3. The appliance of claim 2, wherein the nozzle exit assembly has a pulse fan angle within a range of 5-150°.

4. The appliance of claim 1, wherein the series of gas-injected fluid pulses further comprise a pulsed liquid with a flow rate of 0.15 ml per pulse within a range of 0.05-0.17, with a delivery duration of 0.001-0.5 seconds.

5. The appliance of claim 1, wherein the series of gas-injected fluid pulses further comprise pulsed liquid droplets having a size in a range of –0.002 mm to 3 mm.

* * * * *